United States Patent [19]

Kochar et al.

[11] 4,404,399
[45] Sep. 13, 1983

[54] COPRODUCTION OF ANILINE AND DIPHENYLAMINE

[75] Inventors: Nand K. Kochar, Bronx; Brian J. Ozero, New York, both of N.Y.

[73] Assignee: The Halcon SD Group, Inc., New York, N.Y.

[21] Appl. No.: 431,532

[22] Filed: Sep. 30, 1982

[51] Int. Cl.³ .............................................. C07C 85/06
[52] U.S. Cl. .................................................... 564/402
[58] Field of Search ........................................ 564/402

[56] References Cited

U.S. PATENT DOCUMENTS

| | | | |
|---|---|---|---|
| 1,980,102 | 11/1934 | Semon | 564/402 |
| 2,041,782 | 5/1936 | Semon | 564/402 |
| 2,503,712 | 4/1950 | Clemens et al. | 564/402 |
| 3,272,865 | 9/1966 | Barker | 564/402 |
| 3,418,373 | 12/1968 | Summers et al. | 564/402 X |
| 3,578,714 | 5/1971 | Russell | 564/402 |
| 3,658,906 | 4/1972 | Cryer et al. | 564/402 |
| 4,017,544 | 4/1977 | Mullins | 564/402 X |
| 4,196,147 | 4/1980 | Decker et al. | 564/402 |

Primary Examiner—Paul F. Shaver
Attorney, Agent, or Firm—William C. Long; Riggs T. Stewart; Harold N. Wells

[57] ABSTRACT

A process for the coproduction of aniline and diphenylamine from phenol and ammonia is shown. An aniline reaction mixture containing ammonia and phenol is at least partially reacted to form aniline and that reaction mixture is distilled to separate a portion of the product aniline and the unreacted phenol therein. Aniline and phenol are then at least partially reacted to form diphenylamine. Product aniline and diphenylamine are recovered.

In the preferred embodiment the aniline formed in the aniline reaction is stripped of ammonia and water and distilled to form purified aniline and a crude bottoms product containing phenol and aniline. The latter stream is combined with the dried effluent from the diphenylamine reactor and, after distillation to separate crude diphenylamine, is recycled to the diphenylamine reactor.

7 Claims, 1 Drawing Figure

COPRODUCTION OF ANILINE AND DIPHENYLAMINE

BACKGROUND OF THE INVENTION

This invention relates to the preparation of aniline and diphenylamine. More particularly, it relates to an integrated process for the coproduction of aniline and diphenylamine from phenol and ammonia. Even more particularly, it relates to a novel process wherein an aniline plant and diphenylamine plant are integrated to obtain maximum economic and technical advantage.

Aniline is a commercial chemical of great industrial importance. Its uses are varied and include application as rubber accelerators, antioxidants, dyes, dye intermediates, drug intermediates, explosives and fuel. Conventionally, aniline is prepared by the reduction of nitrobenzene with iron filings or borings and 30% hydrochloric acid; by reaction of chlorobenzene with aqueous ammonia at 200° C. and 800 p.s.i.; and by catalytic vapor phase reduction of nitrobenzene with hydrogen.

It is also known that high yields of aniline can be obtained from phenol by catalytic exchange of the hydroxy radical for the amino radical in the presence of ammonia. This reaction requires a solid catalyst, preferably an alumina or silica-alumina catalyst as is disclosed in U.S. Pat. No. 3,272,865, U.S. Pat. No. 3,578,714 and U.S. Pat. No. 3,860,650. Reaction conditions usually employed are those disclosed in the aforesaid patents and include temperatures between about 300° C. and 600° C. Reaction pressures are superatmospheric and are preferably above 7 atmospheres.

Diphenylamine is also a well-known industrial product with many uses, e.g. in the production of antioxidants for elastomers and in the manufacture of azo dyes. Diphenylamine has generally been prepared commercially by catalytically deammoniating or selfcondensing aniline according to the equation:

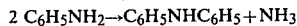

$$2\ C_6H_5NH_2 \rightarrow C_6H_5NHC_6H_5 + NH_3$$

as shown, for example in British Pat. No. 752,859 and in U.S. Pat. Nos. 3,071,619, 2,447,044, 2,645,662 and 3,944,613.

It is also known to produce diphenylamine by catalytically reacting aniline with phenol by the reaction

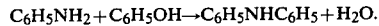

$$C_6H_5NH_2 + C_6H_5OH \rightarrow C_6H_5NHC_6H_5 + H_2O.$$

Such a process is described, for example, in U.S. Pat. No. 2,824,137 which employs titanium catalysts, in British Pat. No. 1,541,153 which uses phosphoric acid as a catalyst, and in Japanese Patent Publication No. 75/07,061 which employs an alumina catalyst. Best results are obtained by reacting phenol and aniline in the presence of an acidic alumina-containing catalyst and especially alumina-silica catalysts containing 5–95% silica as disclosed in U.S. Pat. No. 3,860,650.

Heretofore, to produce diphenylamine from aniline and phenol, it has been necessary to first produce purified aniline and then react the aniline with phenol. To efficiently produce purified aniline it is necessary to maintain a substantial stoichiometric excess of ammonia with respect to phenol in the aniline reaction step. The excess of ammonia is conducive to a fast and selective reaction of ammonia with phenol. Substantial capital and processing expenditures are required, however, for the distillation separation of ammonia from the effluent of the aniline reactor and recycle of the excess ammonia to that reactor.

The process for preparing purified aniline further includes the distillation of the crude aniline reactor effluent from which ammonia and water have been removed, into an overhead aniline product and a bottoms product which comprises an azeotrope of aniline and phenol together with minor but significant amounts of byproduct diphenylamine. The latter byproduct stream is then distilled to separate a phenol-aniline overhead stream which is recycled to the aniline reactor and a bottoms stream containing diphenylamine.

The diphenylamine process has a number of features in common with the aniline process, among them, the following. Phenol is a reactant common to each process; the diphenylamine reaction, like the aniline reaction, is an equilibrium reaction which does not go to completion with the result that unreacted phenol is found in the effluent from both reactors; and diphenylamine can be recovered in purified form from the aniline plant as in the diphenylamine plant although in substantially smaller amounts.

These and other common features of the two processes have been found to lend themselves to an overall integration of the two processes with major and unexpected technical and cost advantages to both process plants.

OBJECTS OF THE INVENTION

It is a primary object of this invention to provide a process for the coproduction of aniline and diphenylamine from phenol and ammonia wherein both products are economically produced from a single process plant.

It is a further and related object of this invention to reduce the capital and processing costs of an aniline plant by reducing the excess of ammonia used in the aniline reaction and by reducing the amount of unreacted ammonia which must be recovered and recycled to the aniline reaction.

It is a further and related object of this invention to reduce the capital and processing costs attendant to the recovery and recycle of unconverted phenol in an aniline plant.

It is a further and related object of this invention to significantly reduce the cost of recovering byproduct diphenylamine from an aniline plant.

It is still a further object of this invention to provide an integrated process for the coproduction of aniline and diphenylamine from phenol and ammonia which is flexible and technically efficient.

SUMMARY OF THE INVENTION

These and other objects of the invention are obtained in a process for the coproduction of aniline and diphenylamine from phenol and ammonia wherein an aniline reaction mixture containing ammonia and phenol is formed, that mixture is at least partially reacted in the presence of a catalyst and under aniline forming conditions to form a mixture containing aniline and unreacted ammonia and phenol, at least a portion of the crude aniline and the unreacted phenol is reacted to make diphenylamine, and product aniline and diphenylamine are recvered from the aniline reaction effluent and the diphenylamine reaction effluent, respectively.

The invention is further described in detail in connection with the drawing.

In the drawing:

FIG. 1 is a simplied process flow sheet showing representative embodiments of the process for the coproduction of aniline and diphenylamine according to the invention.

Referring to FIG. 1, reference numeral 10 identifies the aniline part of the process and reference numeral 12 identifies the diphenylamine part of the process. An aniline reaction mixture 14 is supplied to aniline reactor 16. Aniline reaction mixture 14 is comprised of feed and recycle ammonia streams 18 and 20, respectively and feed and recycle phenol streams, 22 and 24, respectively.

Aniline reaction mixture 14 is passed through aniline reactor 16 and at least partially reacted therein under aniline reaction forming conditions as are more fully described below. An aniline reaction effluent mixture 26 is thereby formed. Mixture 26 contains aniline, unreacted ammonia and phenol, byproduct water and minor amounts of diphenylamine. Effluent mixture 26 is then fed to ammonia column 28 wherein ammonia is stripped from the mixture and recycled via line 20 to aniline reactor 16. The bottoms from ammonia column 28 are passed via line 30 to water column 32 wherein water is stripped from the mixture and removed via line 34.

The ammonia-free and water-free bottoms from column 32 are passed via line 36 and line 38 to aniline column 40. A further portion of the ammonia-free and water-free mixture may pass via line 42 to the diphenylamine plant 12, as is further described below. The mixture of aniline, phenol and minor amounts of diphenylamine introduced into column 40 are separated into an overhead stream comprising purified aniline 44, and a bottoms stream 46 comprising an azeotropic mixture of aniline and phenol and diphenylamine. The "azeotropic" mixture contains an excess of aniline so that the ratio of aniline to phenol is by weight approximately 3–4:1. The use of the term "azeotropic" mixture hereinafter will, therefore, refer to such a mixture rather than a theoretical azeotropic mixture.

The azeotrope and diphenylamine mixture then passes via line 48 to azeotrope recycle column 50. A portion of the azeotrope mixture may pass via line 52 to diphenylamine plant 12, as is further discussed below. Reference numeral 54 identifies an intermediate stream taken from aniline column 40 and containing a mixture of aniline and phenol which optionally may also be supplied to diphenylamine plant 12, as is further described below.

The azeotropic mixture of aniline and phenol supplied to azeotrope recycle column 50 is separated into an overhead stream 56 containing phenol and aniline which joins phenol feed stream 22. A portion of the recycle phenol-aniline mixture may be passed via line 58 to the diphenylamine plant 12, as is further discussed below. The bottoms from azeotrope recycle column 50, containing diphenylamine pass via lines 60 and 62 to the plant limits. A portion of the bottoms from column 50 may be passed via line 64 to the diphenylamine plant 12 as is also further discussed below.

Turning now to diphenylamine plant 12, reference numeral 70 refers to a storage tank containing recycle aniline and phenol. Aniline and phenol from tank 70 and fresh feed phenol pass via lines 72 and 74 respectively, to line 76 and thence to diphenylamine reactor preheater 78. The heated mixture then passes via line 80 to stream preheater 82 and then via line 84 to diphenylamine reactor 86. The aniline and phenol in stream 84 are at least partially reacted in reactor 86 under diphenylamine reaction conditions as are more fully described below. The hot effluent passes via line 88 through heat exchanger 78 in countercurrent heat exchange relationship with feed stream 76 and thence via line 92 to drying column 94 for removal of the water contained in it. Water is removed both in column 32 and in column 94 by conventional azeotropic distillation with a water-immiscible entrainer, e.g. a hydrocarbon. Particularly preferred is toluene. As shown in the case of column 94, the water-entrainer azeotrope is phase-separated in a separator, such as unit 95, with the water being withdrawn from the bottom and the entrainer being returned to the column as reflux.

The bottoms from drying column 94 containing diphenylamine and unreacted aniline and phenol pass via line 120 to recycle column 122. A further feed to column 122 enters via line 124. Stream 124 is comprised of one or more of streams 42, 52, 54, 58 and 64. Each of these streams is provided with a valve designated by reference numerals 42a, 52a, 54a, 58a and 64a, respectively, by which means the flow through the respective lines can be controlled to optimally balance the overall feed 124 to diphenylamine plant 12 generally and to recycle column 122 particular.

In the preferred embodiment of the invention a major portion of the feed 124 emanating from aniline plant 10 is the water and ammonia-free mixture of aniline, phenol and diphenylamine formed in drying column 32 and supplied via line 42. In other embodiments of the invention the feed 124 is a portion of the azeotrope-diphenylamine mixture formed as the distillation bottoms product from aniline column 40 and supplied via line 52 or an intermediate cut 54 taken from aniline column 40 and supplied via line 54. Further amounts of phenol and aniline may be supplied via line 58 and diphenylamine in the bottoms of azeotrope recycle column 50 is supplied via line 64. The latter expedient obviates the necessity of separately purifying the minor amounts of diphenylamine formed in aniline plant 10. Combinations of any or all of streams 42, 52, 54, 58 and 64 may be made as conditions dictate.

The supply of phenol, aniline and minor amounts of diphenylamine from aniline plant 10 to diphenylamine plant 12 via line 42 has the major advantage of decreasing the load on aniline column 40 and azeotrope recycle column 50. Thus aniline, phenol and minor amounts of diphenylamine can be passed immediately to the diphenylamine plant where they enter the recycle column 122 and are joined by the water-free aniline, phenol and diphenylamine mixture in line 120. Likewise, supplying aniline and phenol to diphenylamine plant 12 via either line 52 or a combination of lines 54 and 52 reduces the loads on the aniline column 40 and azeotrope recycle column 50 and decreases the amount of phenol and aniline which otherwise need by recycled via line 24 to aniline reactor 16. Any diphenylamine formed in aniline reactor 16 is not separately worked up but rather passed to diphenylamine plate 12.

The overhead from recycle column 122 comprises aniline and phenol. That stream passes via line 126 to recycle tank 70. The bottoms from recycle column 122, containing diphenylamine and any intermediate by-products which may be present pass via line 128 to intermediates column 130. The overhead stream 132 from intermediates column 130 comprises byproduct compounds which are removed from plant limits. The bottoms stream 134 comprising crude diphenylamine passes to diphenylamine column 136 wherein it is separated into a purified diphenylamine product 138 and a bottoms product 140 which is removed from plant limits.

There are several important and unexpected advantages obtained by integrating aniline plant 10 and diphenylamine plant 12, e.g. vial lines 42, 52, 54, 58 and/or 64. To the extent that the ammonia-free and water-free effluent from aniline reactor 16 passes via line 42 to the diphenylamine plant there is a reduction in the capital cost and processing cost attendant to the operation of aniline column 40 and azeotrope recycle column 50. Any diphenylamine byproduct in stream 42 is recovered in diphenylamine plant 12. The size of columns 40 and 50 and the utilities necessary to operate those columns are substantially reduced as compared with an aniline plant wherein all of the aniline intended for use in a diphenylamine plant is purified in an aniline column and wherein all of the phenol employed in the aniline plant is recycled within that plant. Similarly, where phenol and aniline are supplied to diphenylamine plant 12 via either of lines 52 or 54, the costs attendant to the construction and operation of azeotrope recycle column 50 are substantially decreased. Supplying the bottoms from azeotrope column 50 via line 64 obviates the necessity from separately working up diphenylamine byproduct produced in the aniline plant.

A major advantage of the combined operation described in FIG. 1 is that it is possible by such integration to operate the aniline plant under conditions which would not be possible if the sole product were to be aniline. In order to maintain high reactor efficiency and reaction selectivity to aniline it is necessary to operate an aniline reactor with a substantial excess of ammonia with respect to phenol. This is a costly step both insofar as the reactor and the ammonia column are concerned. With the integrated process of the invention, however, it is possible to conduct the aniline reaction in the presence of substantially smaller excesses of ammonia with respect to phenol. While this results in less efficient production of aniline and higher production of diphenylamine, both consequences are acceptable in the integrated plant because a portion of the crude aniline and phenol are passed directly to the diphenylamine plant for further processing and any diphenylamine contained therein is not lost nor need it be separately recovered. A related advantage is that an existing aniline plant which is combined with a new diphenylamine plant according to the invention becomes debottlenecked insofar as the aniline reactor is concerned. Any unconverted phenol and diphenylamine are reacted and recaptured, respectively, in the diphenylamine plant. The overall advantage of the combined process is substantially reduced capital cost and expenditures for utilities in operation of the plant.

DETAILED DESCRIPTION OF THE ANILINE REACTION

Figure 1:
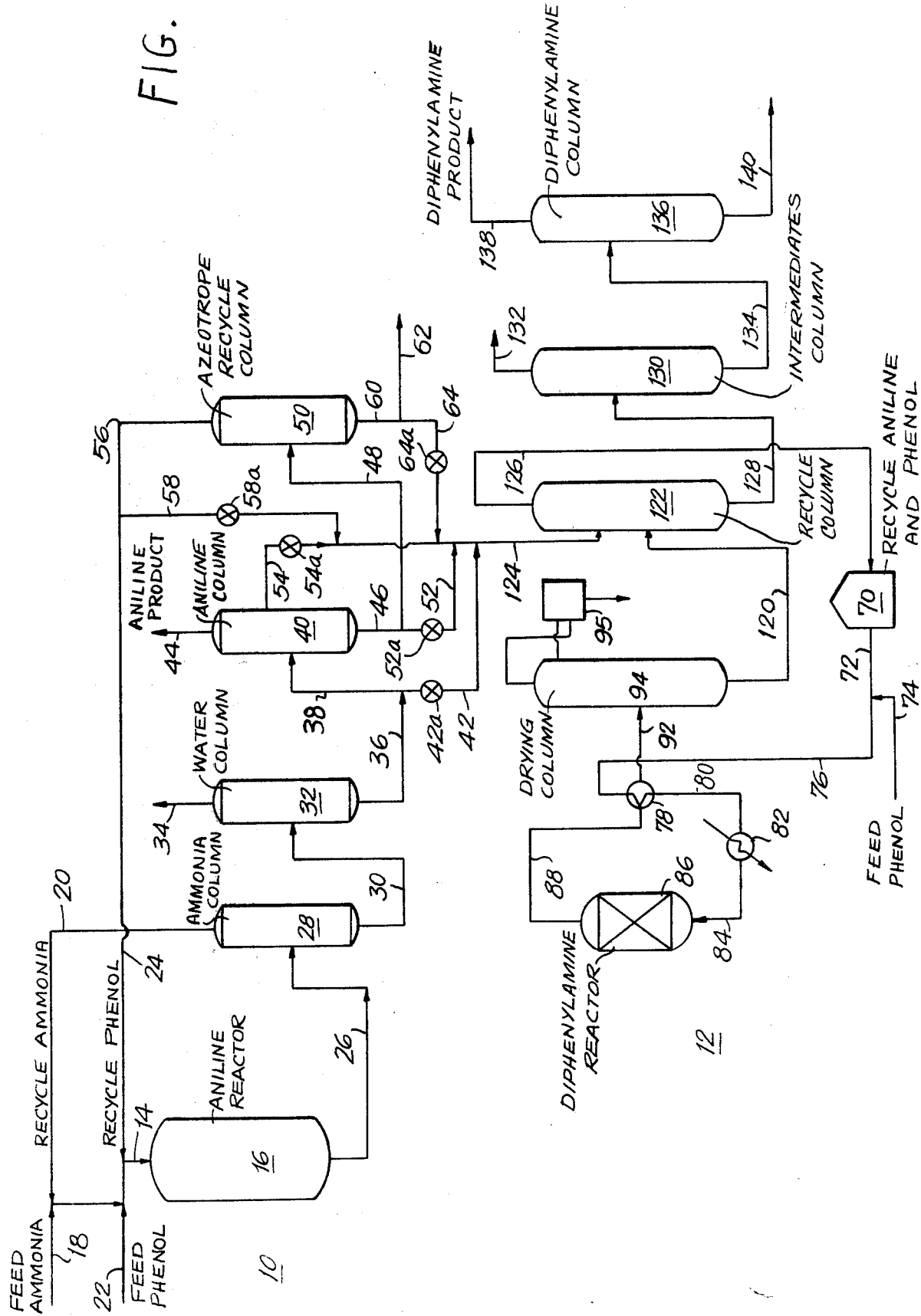

The reaction in aniline reactor 16 takes place in the vapor phase in the presence of a catalyst which may be an alumina, silica-alumina, titania-alumina, zirconia-alumina, phosphoric acid or tungsten oxide, including the silica-alumina acid form zeolites, either natural or synthetic, e.g. molecular sieves. Outstanding results are obtained with silica-alumina catalysts wherein either the silica or the alumina constitutes from 10 to 20% by weight of the catalyst. These catalysts are more strongly acidic than catalysts outside of these compositions and are more effective for the aniline reaction. A highly-effective catalyst is that described in Becker et al. U.S. Pat. No. 3,860,650.

The reaction temperatures which are employed broadly range from 300° to 600° C. are preferably 350° to 500° C. and most desirably are 400° to 480° C. A broad range of pressures may be employed. Preferably, superatmospheric pressures in excess of 7 atmospheres are employed.

The ammonia is used in stoichiometric excess with respect to the phenol. Broadly the ammonia is used in from 1 to 40 moles per mole of phenol and preferably in from 10 to 25 moles per mole of phenol.

Further details relating to the preparation of the catalyst materials and the regeneration of them after use may be found in U.S. Pat. Nos. 3,272,865, 3,578,714 and 3,860,650.

DETAILED DESCRIPTION OF THE DIPHENYLAMINE REACTION

Diphenylamine reactor 86 is a fixed bed reactor containing an acidic solid heterogeneous catalyst, preferably an acidic alumina-silica catalyst containing 5 to 95% silica. Reaction takes place in the liquid phase at a temperature broadly in the range 300°–425° C. and preferably in the range of 320°–400° C. Best results are obtained when the temperature is in the range of 330°–385° C. While lower temperatures can be employed, they tend to reduce the reaction rate to an uneconomic level and while higher temperatures can also be used, they are accompanied by greater byproduct formation.

In order to maintain the aforesaid temperature conditions, pressures of 300 to 800 p.s.i.g. are typically employed. Pressure is not critical but must be maintained at a level sufficient to maintain the liquid phase.

The phenol and aniline may both be present in a 1:1 stoichiometric ratio or either may be present in a molar excess. Ordinarily the molar excess does not exceed 2:1.

The feed stream is passed upwardly and continuously through the catalyst bed. The feed rate may vary over a wide range but desirably the pseudo space velocity is 0.1 to 5 hr$^{-1}$. Selectivities as high as 98% or higher are achieved with significant conversions of the reactants.

Diphenylamine catalysts for use in reactor 86 can be produced by processes well known in the art. For example, the preferred silica-alumina catalyst can be prepared by the procedures described in Chapter 7 of Volume 1 of "Catalysis" edited by Paul H. Emmet (Reinhold Publishing Corporation, New York, 1954), in particular by the procedures described on pages 341–342. The desired ratio of silica to alumina in the catalyst is readily obtained by appropriately varying the amount of the siliceous and aluminous reagents reacted in the described procedure, as will be apparent to persons skilled in the art. Other acidic heterogeneous catalysts which may be used in the diphenylamine reactor are titania-alumina, silica-alumina coated with ceria, silica-alumina coated with $V_2O_5$, zirconia-silica and zirconia-alumina.

It will be obvious that various changes and modifications may be made in the foregoing description of illustrative embodiments of the invention without departing from the invention as defined in the appended claims. For example, as an illustration, the products from the aniline reactor and the diphenylamine reactor could be combined and processed together to recover pure aniline and pure diphenylamine as products and separate water, unreacted phenol and ammonia and any by-products for recycle or disposal, as desired. In reference to the FIG. 1, in such an operation, one could replace the two water columns, 32 and 94, by a single distillation column. Similarly, the azeotrope recycle column 50 would not be needed.

What is claimed is:

1. A process for the coproduction of aniline and diphenylamine from phenol and ammonia comprising the steps of
   (a) forming an aniline reaction mixture containing ammonia and phenol;
   (b) at least partially reacting said aniline reaction mixture in the presence of a catalyst and under aniline forming conditions and thereby forming an aniline reaction effluent mixture containing aniline, water and unreacted ammonia and phenol;
   (c) separating at least a portion of said unreacted phenol and aniline formed in step (b) and at least partially reacting then under diphenylamine forming conditions to form a mixture containing diphenylamine and unreacted aniline and phenol;
   (d) recovering product aniline from the said aniline reaction effluent mixture; and
   (e) recovering product diphenylamine from the mixture formed in step (c).

2. A process for the coproduction of aniline and diphenylamine from phenol and ammonia comprising the steps of
   (a) forming an aniline reaction mixture containing ammonia and phenol;
   (b) at least partially reacting said aniline reaction mixture in the presence of a catalyst and under aniline forming conditions and thereby forming an aniline reaction effluent mixture containing aniline and unreacted ammonia and phenol;
   (c) removing ammonia from said aniline reaction effluent mixture and recycling said ammonia to said aniline forming reaction step (b);
   (d) distilling at least a portion of the aniline and unreacted phenol to form (1) a purified aniline product, and (2) a mixture of phenol and aniline;
   (e) forming a diphenylamine reaction mixture of aniline and phenol from at least one of the ammonia-free aniline reaction effluent mixture and the mixture of aniline and phenol formed in step (d) (2) containing said components and at least partially reacting said diphenylamine reaction mixture under diphenylamine forming conditions to form a reaction effluent mixture containing diphenylamine and unreacted aniline and phenol;
   (f) distilling the diphenylamine and unreacted aniline and phenol from step (e) to form (1) crude diphenylamine, and (2) a mixture of unreacted aniline and phenol;
   (g) recycling said mixture of unreacted aniline and phenol to said diphenylamine reaction step; and
   (h) purifying said crude diphenylamine.

3. A process as recited in claim 2 wherein a portion of the phenol recovered in step (d) (2) is recycled to said aniline forming step and a portion is used to form said diphenylamine reaction mixture.

4. A process for the coproduction of aniline and diphenylamine from phenol and ammonia comprising the steps of
   (a) forming an aniline reaction mixture of ammonia and phenol and at least partially reacting said mixture in the presence of a catalyst and under aniline forming conditions and thereby forming an aniline reaction effluent mixture containing aniline, water, diphenylamine and unreacted ammonia and phenol;
   (b) removing ammonia from said reaction effluent mixture and recycling said ammonia to said aniline forming reaction in step (a) and removing water from said reaction effluent mixture;
   (c) distilling at least a portion of the remaining mixture containing aniline and unreacted phenol and diphenylamine to form (1) a purified aniline product, (2) a mixture of phenol and aniline and (3) a concentrated diphenylamine stream.
   (d) forming a diphenylamine reaction mixture comprising aniline and phenol from at least one of said ammonia-free and water-free stream formed in step (b) and the mixture formed in step (c) (2) and (c) (3), and at least partially reacting said diphenylamine reaction mixture under diphenylamine forming conditions to form a diphenylamine reaction effluent mixture containing diphenylamine and unreacted aniline and phenol;
   (e) distilling the diphenylamine reaction effluent mixture from step (d) to form (1) crude diphenylamine, and (2) a mixture of unreacted aniline and phenol;
   (f) recycling said mixture of unreacted aniline and phenol to said diphenylamine reaction step; and
   (g) purifying said crude diphenylamine.

5. A process as recited in claim 4 wherein said mixture of aniline and phenol from step (c) (2) is an azeotropic mixture formed as a distillation product during the distillation of aniline.

6. A process as recited in claim 4 wherein said mixture of aniline and phenol from step (c) (2) is a crude mixture of said components formed as an intermediate product during the distillation of aniline.

7. A process as recited in claim 4 wherein said mixture of phenol and aniline formed in step (c) (2) is combined with the diphenylamine reaction effluent and said combined stream is distilled as in step (e) to form (1) crude diphenylamine, and (2) a mixture of aniline and phenol for recycle to said diphenylamine reaction step.

* * * * *

UNITED STATES PATENT AND TRADEMARK OFFICE
CERTIFICATE OF CORRECTION

PATENT NO. : 4,404,399
DATED : Sept. 13, 1983
INVENTOR(S) : Nand K. Kochar et al It is certified that error appears in the above-identified patent and that said Letters Patent is hereby corrected as shown below:

Col. 7, line 23 - delete "the"

Col. 8, line 5 - after "phenol" add --and aniline mixture--

Col. 8, line 30 - change "mixture" to --mixtures-- and "step" to --steps--

Signed and Sealed this

Twenty-seventh Day of March 1984

[SEAL]

Attest:

GERALD J. MOSSINGHOFF

Attesting Officer  Commissioner of Patents and Trademarks